(12) United States Patent
Ring et al.

(10) Patent No.: US 11,344,681 B2
(45) Date of Patent: May 31, 2022

(54) DRUG DELIVERY DEVICE

(71) Applicant: AMGEN INC., Thousand Oaks, CA (US)

(72) Inventors: Lawrence S. Ring, Valencia, CA (US); Dhairya Mehta, South San Francisco, CA (US); Stephanie Toy, Moorpark, CA (US); Ferry Tamtoro, Newbury Park, CA (US); Alexander Stuart Cairns, Santa Monica, CA (US); Scott R. Gibson, Granada Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 1315 days.

(21) Appl. No.: 15/047,835

(22) Filed: Feb. 19, 2016

(65) Prior Publication Data
US 2016/0166762 A1 Jun. 16, 2016

Related U.S. Application Data

(63) Continuation of application No. 14/443,847, filed as application No. PCT/US2013/070929 on Nov. 20, 2013.

(Continued)

(51) Int. Cl.
*A61M 5/32* (2006.01)
*A61M 25/02* (2006.01)
(Continued)

(52) U.S. Cl.
CPC ......... *A61M 5/3291* (2013.01); *A61K 9/0019* (2013.01); *A61K 38/193* (2013.01);
(Continued)

(58) Field of Classification Search
CPC .. A61M 5/3291; A61M 5/14; A61M 5/14216; A61M 5/14248; A61M 5/158;
(Continued)

(56) References Cited

U.S. PATENT DOCUMENTS 2,748,769 A 6/1956 Huber
3,408,846 A 11/1968 Schofield
(Continued)

FOREIGN PATENT DOCUMENTS

CA 2779793 A1 5/2011
EP 1543854 A1 6/2005
(Continued)

OTHER PUBLICATIONS

"G-CSF." The Scott Hamilton CARES Initiative, Chemo Care, Nov. 5, 2012, web.archive.org/web/20121105231147/chemocare.com/chemotherapy/drug-info/g-csf.aspx. (Year: 2012).*
(Continued)

*Primary Examiner* — James D Ponton
(74) *Attorney, Agent, or Firm* — Marshall, Gerstein & Borun LLP

(57) ABSTRACT

A drug delivery device includes a blunt cannula and a reservoir. The blunt cannula has a cylindrical wall that defines an axial passage between a first end and a second end of the blunt cannula. The wall has at least a first tapered region at the first end to define an opening in fluid communication with the axial passage and adapted at the first end to resist interruption of fluid flow through the axial passage and out of the first end of the blunt cannula. The reservoir is connected to the second end of the blunt cannula.

19 Claims, 5 Drawing Sheets

Related U.S. Application Data

(60) Provisional application No. 61/774,567, filed on Mar. 7, 2013, provisional application No. 61/729,303, filed on Nov. 21, 2012.

(51) Int. Cl.

| | | |
|---|---|---|
| *A61M 5/142* | (2006.01) | |
| *A61M 5/20* | (2006.01) | |
| *A61M 5/42* | (2006.01) | |
| *A61M 25/00* | (2006.01) | |
| *A61M 5/14* | (2006.01) | |
| *A61M 5/31* | (2006.01) | |
| *A61M 5/30* | (2006.01) | |
| *C12N 9/64* | (2006.01) | |
| *C07K 14/535* | (2006.01) | |
| *A61K 38/19* | (2006.01) | |
| *A61K 38/28* | (2006.01) | |
| *A61K 38/26* | (2006.01) | |
| *A61M 5/158* | (2006.01) | |
| *A61K 9/00* | (2006.01) | |

(52) U.S. Cl.
CPC .............. *A61K 38/26* (2013.01); *A61K 38/28* (2013.01); *A61M 5/14* (2013.01); *A61M 5/14216* (2013.01); *A61M 5/14248* (2013.01); *A61M 5/158* (2013.01); *A61M 5/20* (2013.01); *A61M 5/3134* (2013.01); *A61M 5/3286* (2013.01); *A61M 5/3287* (2013.01); *A61M 5/422* (2013.01); *A61M 25/007* (2013.01); *A61M 25/0015* (2013.01); *A61M 25/0068* (2013.01); *A61M 25/02* (2013.01); *C07K 14/535* (2013.01); *C12N 9/6424* (2013.01); *A61M 2005/1401* (2013.01); *A61M 2005/1585* (2013.01); *A61M 2005/3022* (2013.01); *A61M 2005/3289* (2013.01); *A61M 2025/0073* (2013.01); *A61M 2202/0007* (2013.01)

(58) Field of Classification Search
CPC .... A61M 5/20; A61M 5/3134; A61M 5/3286; A61M 5/3287; A61M 5/422; A61M 25/0015; A61M 25/0068; A61M 25/007; A61M 25/02; A61M 2005/1585; A61M 2005/3022
See application file for complete search history.

(56) References Cited

U.S. PATENT DOCUMENTS

| | | |
|---|---|---|
| 4,698,058 A | 10/1987 | Greenfeld et al. |
| 4,699,612 A | 10/1987 | Hamacher |
| 4,703,008 A | 10/1987 | Lin |
| 4,717,379 A | 1/1988 | Ekholmer |
| 4,737,152 A | 4/1988 | Alchas |
| 4,976,703 A | 12/1990 | Franetzki et al. |
| 5,064,411 A * | 11/1991 | Gordon, III ........... A61B 42/10 604/48 |
| 5,257,980 A | 11/1993 | Van Antwerp et al. |
| 5,441,868 A | 8/1995 | Lin |
| 5,458,614 A | 10/1995 | Humphrey |
| 5,547,933 A | 8/1996 | Lin |
| 5,618,698 A | 4/1997 | Lin |
| 5,621,080 A | 4/1997 | Lin |
| 5,647,851 A | 7/1997 | Pokras |
| 5,686,292 A | 11/1997 | Schwall et al. |
| 5,756,349 A | 5/1998 | Lin |
| 5,767,078 A | 6/1998 | Johnson et al. |
| 5,773,569 A | 6/1998 | Wrighton et al. |
| 5,789,554 A | 8/1998 | Leung et al. |
| 5,797,882 A | 8/1998 | Purdy et al. |
| 5,830,851 A | 11/1998 | Wrighton et al. |
| 5,856,298 A | 1/1999 | Strickland |
| 5,865,744 A | 2/1999 | Lemelson |
| 5,951,530 A | 9/1999 | Steengaard et al. |
| 5,955,422 A | 9/1999 | Lin |
| 5,986,047 A | 11/1999 | Wrighton et al. |
| 6,030,086 A | 2/2000 | Thomas |
| 6,162,202 A | 12/2000 | Sicurelli et al. |
| 6,264,645 B1 | 7/2001 | Jonkman |
| 6,310,078 B1 | 10/2001 | Connolly et al. |
| 6,346,095 B1 * | 2/2002 | Gross ................... A61M 5/3291 604/272 |
| 6,391,633 B1 | 5/2002 | Stern et al. |
| 6,468,529 B1 | 10/2002 | Schwall et al. |
| 6,583,272 B1 | 6/2003 | Bailon |
| 6,586,398 B1 | 7/2003 | Kinstler et al. |
| 6,595,956 B1 | 7/2003 | Gross et al. |
| 6,702,790 B1 * | 3/2004 | Ross .................... A61M 5/3286 604/239 |
| 6,750,369 B2 | 6/2004 | Connolly et al. |
| 6,756,480 B2 | 6/2004 | Kostenuik et al. |
| 6,803,453 B1 | 10/2004 | Brunkow et al. |
| 6,835,809 B1 | 12/2004 | Liu et al. |
| 6,900,292 B2 | 5/2005 | Sun et al. |
| 6,919,426 B2 | 7/2005 | Boone et al. |
| 6,969,379 B1 | 11/2005 | Aboul-Hosn et al. |
| 7,030,226 B2 | 4/2006 | Sun et al. |
| 7,037,498 B2 | 5/2006 | Cohen et al. |
| 7,084,245 B2 | 8/2006 | Holmes et al. |
| 7,153,507 B2 | 12/2006 | van de Winkel et al. |
| 7,220,410 B2 | 5/2007 | Kim et al. |
| 7,271,689 B1 | 9/2007 | Danby et al. |
| 7,455,663 B2 | 11/2008 | Bikovsky |
| 7,521,048 B2 | 4/2009 | Gliniak et al. |
| 7,588,552 B2 | 9/2009 | Yeshurun et al. |
| 7,766,878 B2 | 8/2010 | Tremaglio, Jr. et al. |
| 7,828,771 B2 | 11/2010 | Chiang et al. |
| 7,857,131 B2 | 12/2010 | Vedrine |
| 8,030,547 B2 | 10/2011 | Kaku et al. |
| 2001/0051798 A1 * | 12/2001 | Hochman ........... A61M 5/3287 604/506 |
| 2002/0123740 A1 * | 9/2002 | Flaherty .............. A61M 5/1452 604/890.1 |
| 2002/0155998 A1 | 10/2002 | Young et al. |
| 2003/0009153 A1 | 1/2003 | Brisken et al. |
| 2003/0023586 A1 | 1/2003 | Knorr |
| 2003/0077753 A1 | 4/2003 | Tischer |
| 2003/0082749 A1 | 5/2003 | Sun et al. |
| 2003/0138421 A1 | 7/2003 | van de Winkel et al. |
| 2003/0143202 A1 | 7/2003 | Binley et al. |
| 2003/0195156 A1 | 10/2003 | Min et al. |
| 2003/0208167 A1 | 11/2003 | Prausnitz et al. |
| 2003/0215444 A1 | 11/2003 | Elliott |
| 2003/0229023 A1 | 12/2003 | Oliner et al. |
| 2003/0235582 A1 | 12/2003 | Singh et al. |
| 2004/0009902 A1 | 1/2004 | Boime et al. |
| 2004/0018191 A1 | 1/2004 | Wang et al. |
| 2004/0071694 A1 | 4/2004 | DeVries et al. |
| 2004/0071702 A1 | 4/2004 | van de Winkel et al. |
| 2004/0086503 A1 | 5/2004 | Cohen et al. |
| 2004/0091961 A1 | 5/2004 | Evans et al. |
| 2004/0097712 A1 | 5/2004 | Varnum et al. |
| 2004/0116865 A1 | 6/2004 | Bengtsson |
| 2004/0122380 A1 | 6/2004 | Utterberg |
| 2004/0143857 A1 | 7/2004 | Young et al. |
| 2004/0157293 A1 | 8/2004 | Evans et al. |
| 2004/0175379 A1 | 9/2004 | DeVries et al. |
| 2004/0175824 A1 | 9/2004 | Sun et al. |
| 2004/0181033 A1 | 9/2004 | Han et al. |
| 2004/0202655 A1 | 10/2004 | Morton et al. |
| 2004/0228859 A1 | 11/2004 | Graus et al. |
| 2004/0229318 A1 | 11/2004 | Heavner |
| 2004/0248815 A1 | 12/2004 | Connolly et al. |
| 2004/0265307 A1 | 12/2004 | Singh et al. |
| 2004/0266690 A1 | 12/2004 | Pool |
| 2005/0004353 A1 | 1/2005 | Welcher et al. |
| 2005/0008642 A1 | 1/2005 | Graus et al. |
| 2005/0019914 A1 | 1/2005 | Staerk et al. |
| 2005/0026834 A1 | 2/2005 | Cox et al. |

(56) References Cited

U.S. PATENT DOCUMENTS

| | | |
|---|---|---|
| 2005/0033265 A1* | 2/2005 | Engel ............... A61B 17/3421 604/523 |
| 2005/0074821 A1 | 4/2005 | Wild et al. |
| 2005/0084906 A1 | 4/2005 | Goetsch et al. |
| 2005/0096461 A1 | 5/2005 | Cox |
| 2005/0107297 A1 | 5/2005 | Holmes et al. |
| 2005/0107591 A1 | 5/2005 | Cox |
| 2005/0112694 A1 | 5/2005 | Carter et al. |
| 2005/0118643 A1 | 6/2005 | Burgess et al. |
| 2005/0124045 A1 | 6/2005 | Sun et al. |
| 2005/0124564 A1 | 6/2005 | Binley et al. |
| 2005/0136063 A1 | 6/2005 | Wang et al. |
| 2005/0137329 A1 | 6/2005 | Holmes et al. |
| 2005/0142642 A1 | 6/2005 | Sun et al. |
| 2005/0143292 A1 | 6/2005 | DeFrees et al. |
| 2005/0153879 A1 | 7/2005 | Svetina et al. |
| 2005/0158822 A1 | 7/2005 | Pecker |
| 2005/0158832 A1 | 7/2005 | Young et al. |
| 2005/0170457 A1 | 8/2005 | Pool et al. |
| 2005/0177117 A1 | 8/2005 | Crocker et al. |
| 2005/0181359 A1 | 8/2005 | Optelten et al. |
| 2005/0181482 A1 | 8/2005 | Meade et al. |
| 2005/0186203 A1 | 8/2005 | Singh et al. |
| 2005/0192211 A1 | 9/2005 | Gillies et al. |
| 2005/0202538 A1 | 9/2005 | Gillies et al. |
| 2005/0203461 A1 | 9/2005 | Flaherty et al. |
| 2005/0215006 A1 | 9/2005 | Horii et al. |
| 2005/0227289 A1 | 10/2005 | Reilly et al. |
| 2005/0244408 A1 | 11/2005 | Cohen et al. |
| 2005/0244409 A1 | 11/2005 | Erickson-Miller et al. |
| 2005/0249728 A1 | 11/2005 | Singh et al. |
| 2005/0273076 A1 | 12/2005 | Beasley et al. |
| 2006/0040358 A1 | 2/2006 | Ligensa et al. |
| 2006/0040858 A1 | 2/2006 | Holmes et al. |
| 2006/0088906 A1 | 4/2006 | DeFrees et al. |
| 2006/0111279 A1 | 5/2006 | DeFrees et al. |
| 2006/0135431 A1 | 6/2006 | Min et al. |
| 2007/0110747 A1 | 5/2007 | Paszty et al. |
| 2007/0129688 A1 | 6/2007 | Scheurer et al. |
| 2007/0253951 A1 | 11/2007 | Ng et al. |
| 2008/0039796 A1 | 2/2008 | Nakajima |
| 2008/0051714 A1 | 2/2008 | Moberg et al. |
| 2008/0051730 A1* | 2/2008 | Bikovsky ............ A61M 5/14248 604/240 |
| 2008/0077081 A1 | 3/2008 | Mounce et al. |
| 2008/0166352 A1 | 7/2008 | Siu et al. |
| 2008/0172012 A1 | 7/2008 | Hiniduma-Lokuge et al. |
| 2008/0215006 A1* | 9/2008 | Thorkild ............ A61M 5/14248 604/151 |
| 2008/0269682 A1 | 10/2008 | Kavazov et al. |
| 2008/0281250 A1 | 11/2008 | Bergsneider et al. |
| 2008/0294096 A1 | 11/2008 | Uber, III et al. |
| 2009/0069750 A1 | 3/2009 | Schraga |
| 2009/0234106 A1 | 9/2009 | Han et al. |
| 2009/0246192 A1 | 10/2009 | Condra et al. |
| 2009/0270804 A1 | 10/2009 | Mesa et al. |
| 2009/0287186 A1 | 11/2009 | Adams et al. |
| 2010/0004558 A1 | 1/2010 | Frankhouser et al. |
| 2010/0100045 A1 | 4/2010 | Pravongviengkham et al. |
| 2010/0106104 A1* | 4/2010 | Villette ............... A61M 5/3286 604/272 |
| 2010/0145276 A1* | 6/2010 | Yodfat ............... A61M 5/1413 604/151 |
| 2010/0211011 A1 | 8/2010 | Haar |
| 2010/0324503 A1 | 12/2010 | McKinnon et al. |
| 2011/0097318 A1 | 4/2011 | Gadgil |
| 2011/0144587 A1 | 6/2011 | Stone |
| 2011/0230837 A1 | 9/2011 | Kamen et al. |
| 2012/0136308 A1 | 5/2012 | Racz |
| 2012/0259282 A1* | 10/2012 | Alderete, Jr ...... A61M 5/14244 604/131 |
| 2012/0265166 A1 | 10/2012 | Yodfat |
| 2012/0271123 A1 | 10/2012 | Castle et al. |
| 2012/0277667 A1 | 11/2012 | Yodat et al. |
| 2013/0184541 A1 | 7/2013 | Antonio et al. |
| 2013/0245555 A1 | 9/2013 | Dirac et al. |
| 2013/0253472 A1 | 9/2013 | Cabiri |
| 2014/0127048 A1 | 5/2014 | Dilanni et al. |
| 2014/0288511 A1* | 9/2014 | Tan-Malecki ....... A61M 5/2466 604/244 |
| 2015/0051583 A1* | 2/2015 | Horvath ............ A61M 25/0015 604/508 |
| 2015/0290390 A1 | 10/2015 | Ring et al. |
| 2016/0166762 A1 | 6/2016 | Ring et al. |
| 2016/0199574 A1 | 7/2016 | Ring et al. |
| 2017/0072143 A1 | 3/2017 | Ring et al. |
| 2019/0030242 A1 | 1/2019 | Searle et al. |

FOREIGN PATENT DOCUMENTS

| | | |
|---|---|---|
| GB | 982780 A | 2/1965 |
| JP | S5230695 U | 3/1977 |
| JP | S5944449 U | 3/1984 |
| JP | H023736 U | 1/1990 |
| JP | H1080491 A | 3/1998 |
| JP | 2001178820 A | 7/2001 |
| JP | 2002263188 A | 9/2002 |
| JP | 2004242809 A | 9/2004 |
| JP | 2004532659 A | 10/2004 |
| JP | 2005169012 A | 6/2005 |
| JP | 2005537893 A | 12/2005 |
| JP | 2008043445 A | 2/2008 |
| JP | 2011518024 A | 6/2011 |
| LU | 44182 A1 | 10/1963 |
| WO | WO-91/05867 A1 | 5/1991 |
| WO | WO-95/05465 A1 | 2/1995 |
| WO | WO-96/40772 A2 | 12/1996 |
| WO | WO-9638557 A1 | 12/1996 |
| WO | WO-99/66054 A2 | 12/1999 |
| WO | WO-00/24893 A2 | 5/2000 |
| WO | WO-00/61637 A1 | 10/2000 |
| WO | WO-01/031007 A2 | 5/2001 |
| WO | WO-01/36489 A2 | 5/2001 |
| WO | WO-0181405 A2 | 11/2001 |
| WO | WO-0214356 A2 | 2/2002 |
| WO | WO-02/19963 A2 | 3/2002 |
| WO | WO-02/20034 A1 | 3/2002 |
| WO | WO-02/49673 A2 | 6/2002 |
| WO | WO-02/085940 A2 | 10/2002 |
| WO | WO-03/002713 A2 | 1/2003 |
| WO | WO-03/022337 A1 | 3/2003 |
| WO | WO-03/029291 A2 | 4/2003 |
| WO | WO-03/030833 A2 | 4/2003 |
| WO | WO-03/057134 A2 | 7/2003 |
| WO | WO-03/059951 A2 | 7/2003 |
| WO | WO-0355526 A2 | 7/2003 |
| WO | WO-03/084477 A2 | 10/2003 |
| WO | WO-03/094858 A2 | 11/2003 |
| WO | WO-2004/002417 A2 | 1/2004 |
| WO | WO-2004/002424 A2 | 1/2004 |
| WO | WO-2004/009627 A1 | 1/2004 |
| WO | WO-2004006982 A2 | 1/2004 |
| WO | WO-2004/018667 A1 | 3/2004 |
| WO | WO-2004/024219 A1 | 3/2004 |
| WO | WO-2004/024761 A1 | 3/2004 |
| WO | WO-2004/033651 A2 | 4/2004 |
| WO | WO-2004/035603 A2 | 4/2004 |
| WO | WO-2004/043382 A2 | 5/2004 |
| WO | WO-2004/058988 A2 | 7/2004 |
| WO | WO-2004/101600 A2 | 11/2004 |
| WO | WO-2004/101606 A2 | 11/2004 |
| WO | WO-2004/101611 A2 | 11/2004 |
| WO | WO-2004/106373 A1 | 12/2004 |
| WO | WO-2005/001025 A2 | 1/2005 |
| WO | WO-2005/001136 A1 | 1/2005 |
| WO | WO-05/016970 A2 | 2/2005 |
| WO | WO-2005/017107 A2 | 2/2005 |
| WO | WO-2005/021579 A2 | 3/2005 |
| WO | WO-2005/025606 A1 | 3/2005 |
| WO | WO-2005/032460 A2 | 4/2005 |
| WO | WO-2005/047331 A2 | 5/2005 |
| WO | WO-05/058967 A2 | 6/2005 |
| WO | WO-2005/051327 A2 | 6/2005 |

(56) References Cited

FOREIGN PATENT DOCUMENTS

| WO | WO-2005/063808 A1 | 7/2005 |
| --- | --- | --- |
| WO | WO-2005/063809 A1 | 7/2005 |
| WO | WO-2005/070451 A1 | 8/2005 |
| WO | WO-2005/081687 A2 | 9/2005 |
| WO | WO-2005/084711 A1 | 9/2005 |
| WO | WO-2005/092369 A2 | 10/2005 |
| WO | WO-2005/100403 A2 | 10/2005 |
| WO | WO-2005/103076 A2 | 11/2005 |
| WO | WO-2006/02646 A2 | 1/2006 |
| WO | WO-06/013472 A2 | 2/2006 |
| WO | WO-2006/29094 A2 | 3/2006 |
| WO | WO-2006032689 A1 | 3/2006 |
| WO | WO-2006/50959 A2 | 5/2006 |
| WO | WO-2006081171 A1 | 8/2006 |
| WO | WO-06/138729 A2 | 12/2006 |
| WO | WO-07/000328 A1 | 1/2007 |
| WO | WO-07/011941 A2 | 1/2007 |
| WO | WO-07/012614 A2 | 2/2007 |
| WO | WO-2007/136752 A2 | 11/2007 |
| WO | WO-2007128121 A1 | 11/2007 |
| WO | WO-2008/057457 A2 | 5/2008 |
| WO | WO-2008/057458 A2 | 5/2008 |
| WO | WO-2008/057459 A2 | 5/2008 |
| WO | WO-2008/063382 A2 | 5/2008 |
| WO | WO-2008/125623 A2 | 10/2008 |
| WO | WO-2008/133647 A2 | 11/2008 |
| WO | WO-2009/055783 A2 | 4/2009 |
| WO | WO-2009/100297 A1 | 8/2009 |
| WO | WO-2009/100318 A1 | 8/2009 |
| WO | WO-2009/125398 A2 | 10/2009 |
| WO | WO-20090158655 A2 | 12/2009 |
| WO | WO-2010/029513 A2 | 3/2010 |
| WO | WO-2010/077854 A1 | 7/2010 |
| WO | WO-2010/080715 A1 | 7/2010 |
| WO | WO-2011/037791 A1 | 3/2011 |
| WO | WO-2011/053759 A2 | 5/2011 |
| WO | WO-2011/053783 A2 | 5/2011 |
| WO | WO-2011/072263 A1 | 6/2011 |
| WO | WO-2011/111007 A2 | 9/2011 |
| WO | WO-2011156373 | 12/2011 |
| WO | WO-2012/054438 A1 | 4/2012 |
| WO | WO-2012045667 A2 | 4/2012 |
| WO | WO-2012/088313 A1 | 6/2012 |
| WO | WO-2012/101251 A1 | 8/2012 |
| WO | WO-2012/101252 A2 | 8/2012 |
| WO | WO-2012/101253 A1 | 8/2012 |
| WO | WO-2012/108956 A2 | 8/2012 |
| WO | WO-2012/109530 A1 | 8/2012 |
| WO | WO-2012101507 A1 | 8/2012 |
| WO | WO-2013/032647 A1 | 3/2013 |
| WO | WO-2013040247 A2 | 3/2013 |
| WO | WO-2013/103864 A1 | 7/2013 |
| WO | WO-2013/165715 A1 | 11/2013 |

OTHER PUBLICATIONS

Japanese Patent Application No. 2018-124003, Notice of Rejection, dated May 14, 2019.
Office Action issued in U.S. Appl. No. 15/040,372, dated Apr. 10, 2018.
Office Action issued in U.S. Appl. No. 15/347,497, dated Jan. 13, 2017.
Office Action issued in U.S. Appl. No. 15/347,497, dated Jun. 21, 2017.
Office Action issued in U.S. Appl. No. 15/347,497, dated Nov. 17, 2017.
Office Action issued in U.S. Appl. No. 15/347,497, dated May 15, 2018.
Office Action issued in U.S. Appl. No. 14/443,847, dated May 18, 2017.
Office Action issued in U.S. Appl. No. 14/443,847, dated Nov. 9, 2017.
Office Action issued in U.S. Appl. No. 14/443,847, dated Apr. 4, 2018.
Inserting Your Quick-Set Infusion Set [Viewed on internet on Apr. 26, 2018] Viewed on internet. <URL:https://www.youtube.com/watch?v=BfG4-YMu0Vo>, Published on Mar. 11, 2009.
Examination Report No. 3 issued in counterpart Australian Application No. 2013348071, dated Apr. 27, 2018.
Australian Patent Application No. 2013348071, Examination Report No. 2, dated Dec. 15, 2017.
European Patent Application No. 13802787.5, Communication Pursuant to Article 94(3) EPC, dated Nov. 2, 2018.
U.S. Appl. No. 14/443,847, Final Office Action, dated Oct. 17, 2018.
U.S. Appl. No. 15/040,372, Final Office Action, dated Oct. 12, 2018.
U.S. Appl. No. 15/347,497, Nonfinal Office Action, dated Nov. 29, 2018.
Second Official Action dated Apr. 3, 2018 by Japanese Patent Office in counterpart Japanese Patent Application No. 2015-544105, and translation thereof.
Communication Pursuant to Article 94(3) EPC dated Mar. 22, 2018 in counterpart European Patent application No. 13802787.5.
International Search Report for PCT/US2013/070929, dated Feb. 3, 2014.
Extended European Search Report for Application No. EP16155465, dated Aug. 26, 2016.
Extended European Search Report for Application No. EP16156472.9, dated Sep. 15, 2016.
Canadian Patent Application No. 2884887, Office Action, dated Feb. 26, 2019.
European Patent Application No. 16456472.9, Communication Pursuant to Article 94(3) EPC, dated Apr. 15, 2019.
U.S. Appl. No. 14/443,847, Nonfinal Office Action, dated Mar. 20, 2019.
U.S. Appl. No. 15/040,372, Nonfinal Office Action, dated Mar. 21, 2019.
Australian Office Action for Application No. 2013348071, dated May 15, 2017.
Japanese Office Action for Application No. 2015-544105, dated Aug. 22, 2017.
Mexican Patent Application No. MX/a/2015/006343, Office Action, dated Sep. 5, 2019.
Australian Patent Application No. 2018220071, Examination Report No. 1, dated Sep. 23, 2019.
U.S. Appl. No. 15/347,497, Final Office Action, dated Jun. 13, 2019.
U.S. Appl. No. 15/347,497, Nonfinal Office Action, dated Sep. 30, 2019.
U.S. Appl. No. 15/040,372, Final Office Action, dated Oct. 28, 2019.
U.S. Appl. No. 14/443,847, Final Office Action, dated Oct. 29, 2019.
U.S. Appl. No. 16/779,135, Nonfinal Office Action, dated Apr. 6, 2020.
U.S. Appl. No. 14/443,847, Nonfinal Office Action, dated Jun. 9, 2020.
U.S. Appl. No. 16/779,135, Final Office Action, dated Oct. 15, 2020.
U.S. Appl. No. 15/347,497, Final Office Action, dated May 13, 2020.
U.S. Appl. No. 14/443,847, Final Office Action, dated Dec. 8, 2020.
U.S. Appl. No. 14/443,847, Nonfinal Office Action, dated Feb. 23, 2021.
U.S. Appl. No. 15/347,497, Nonfinal Office Action, dated Feb. 5, 2021.
Australian Patent Application No. 2020204525, Examination Report, dated Aug. 19, 2021.
U.S. Appl. No. 16/779,135, Nonfinal Office Action, dated Aug. 9, 2021.
Japanese Patent Application No. 2018-124003 (Appeal No. 2021-002261 against the Examiner's Decision of Rejection), Notice of Rejection, dated Nov. 16, 2021.
U.S. Appl. No. 14/443,847, Nonfinal Office Action, dated Nov. 18, 2021.
U.S. Appl. No. 15/347,497, Nonfinal Office Action, dated Nov. 18, 2021.
Japanese Patent Application No. 2021-025393, Notice of Rejection, dated Nov. 24, 2021.

* cited by examiner

DRUG DELIVERY DEVICE

CROSS-REFERENCE TO RELATED APPLICATION

This is a continuation of U.S. application Ser. No. 14/443,847, filed May 19, 2015, which is the U.S. National Stage of PCT/US2013/070929, filed Nov. 20, 2013, which is an application claiming the benefit of priority of U.S. Provisional Application No. 61/774,567, filed Mar. 7, 2013, and U.S. Provisional Application No. 61/729,303, filed Nov. 21, 2012. The entire contents of each of the foregoing are incorporated herein by reference.

BACKGROUND

This patent is directed to a drug delivery device, and, in particular, to a drug delivery device for use with a blunt cannula or rigid needle.

Drug delivery devices can administer a bolus at high flow rates. Such drug delivery devices include, but are not limited to, autoinjectors, infusion pumps and microinfusers. A microinfuser can be an on-body pump that may be worn continuously. At such high flow rates, the flow of a drug can become interrupted when a buildup of pressure occurs at the tip of the needle or cannula used to administer the bolus. The buildup of pressure may occur when, for example, the opening at the end of the needle or cannula is occluded or blocked. The interruption of the flow through the needle or cannula can have negative effects, such as preventing delivery of the correct amount of drug product or preventing delivery of the drug product at the desired rate (i.e., a lower rate must be used).

SUMMARY

According to an aspect of the present disclosure, a drug delivery device includes a blunt cannula and a reservoir. The blunt cannula has a cylindrical wall that defines an axial passage between a first end and a second end of the blunt cannula. The wall has at least a first tapered region at the first end to define an opening in fluid communication with the axial passage and adapted at the first end to resist interruption of fluid flow through the axial passage and out of the first end of the blunt cannula. The reservoir is connected to the second end of the blunt cannula.

According to another aspect of the present disclosure, a drug delivery device includes a blunt cannula and a reservoir. The blunt cannula has a cylindrical wall that defines an axial passage between a closed first end and a second end of the blunt cannula. The wall has a first tapered region at the first end with at least one side opening in fluid communication with the axial passage adapted to resist interruption of fluid flow through the axial passage and out of the first end of the blunt cannula. The reservoir is connected to the second end of the blunt cannula.

According to a further aspect of the present disclosure, a drug delivery device includes a blunt cannula, a vibration generator, and a reservoir. The blunt cannula has a cylindrical wall that defines an axial passage between a first end and a second end of the blunt cannula. The wall has in a first tapered region at the first end to define an opening in fluid communication with the axial passage. The vibration generator is coupled to the blunt cannula, the generator being actuated to resist interruption of fluid flow through the axial passage and out of the first end of the blunt cannula. The reservoir connected to the second end of the blunt cannula.

According to a still further aspect of the present disclosure, a drug delivery device includes a rigid needle and a reservoir. The rigid needle has a cylindrical wall that defines an axial passage between a first end and a second end of the rigid needle. The wall has an opening at the first end in fluid communication with the axial passage and adapted at the first end to resist interruption of fluid flow through the axial passage and out of the first end of the rigid needle. The adaptation at the first end includes at least one of a pattern of openings disposed about the opening in the first tapered region, and at least one external recessed region recessed toward the axial passage relative to adjoining surface regions. The reservoir is connected to the second end of the rigid needle.

According to yet another aspect of the present disclosure, a drug delivery device includes a rigid needle, a vibration generator and a reservoir. The rigid needle has a cylindrical wall that defines an axial passage between a first end and a second end of the rigid needle. The wall has an opening at the first end in fluid communication with the axial passage. The vibration generator is coupled to the rigid needle, the generator being actuated to resist interruption of fluid flow through the axial passage and out of the first end of the rigid needle. The reservoir is connected to the second end of the rigid needle.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Figure 1:
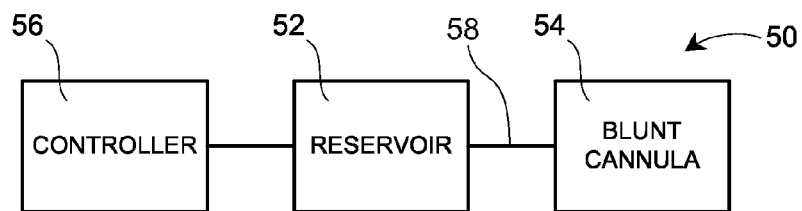
FIG. 1 is a schematic view of a drug delivery device according to the present disclosure, including a blunt cannula adapted to resist interruption of fluid flow through the cannula.

FIG. 1 is a schematic diagram of a drug delivery device 50 according to the present disclosure, which drug delivery device 50 may be in the form of an autoinjector, infuser or microinfuser, for example. For the purpose of clarification, reference to one of these devices does not preclude use of other drug delivery devices. The drug delivery device 50 includes a reservoir 52 and a blunt cannula 54. The blunt cannula 54 has a first end and a second end, the reservoir 52 connected to the second end of the blunt cannula 54 and the first end used for subcutaneous delivery of a drug product from the reservoir to a patient. The reservoir can be any primary container, e.g. a prefilled syringe or a cartridge. The drug delivery device 50 also includes a controller 56 that is operatively coupled to the reservoir 52, and may even preferably be formed integrally with the reservoir 52. The controller 56 may include a drive, which may be mechanical, electromechanical, or electrical, that is operatively coupled to the reservoir 52 to force fluid from the reservoir 52 through the blunt cannula 54. For example, where the reservoir 52 is defined by a barrel and a plunger disposed within the barrel, the drive may incorporate a mechanical element that advances the plunger along the barrel to force a drug product from the reservoir 52. The controller 56 may also include a microprocessor which is operatively coupled to the drive to cause the drive to actuate. In some embodiments, the controller 56 may simply be a plunger rod in a syringe.

FIGS. 2-14 illustrate a variety of blunt cannulas according to the present disclosure. In particular, FIGS. 2-5 illustrate one embodiment of a blunt cannula, the details of which are discussed so that the structure and function of the remaining embodiments illustrated in FIGS. 6-15 might be appreciated without repeating the details of structure and function common with the embodiment of FIGS. 2-5 for each of these additional embodiments. Instead, only the details of structure and function that differentiate the embodiments illustrated in FIGS. 6-15 from the embodiment of FIGS. 2-5 will be discussed in relation to FIGS. 6-15.

Figure 2:
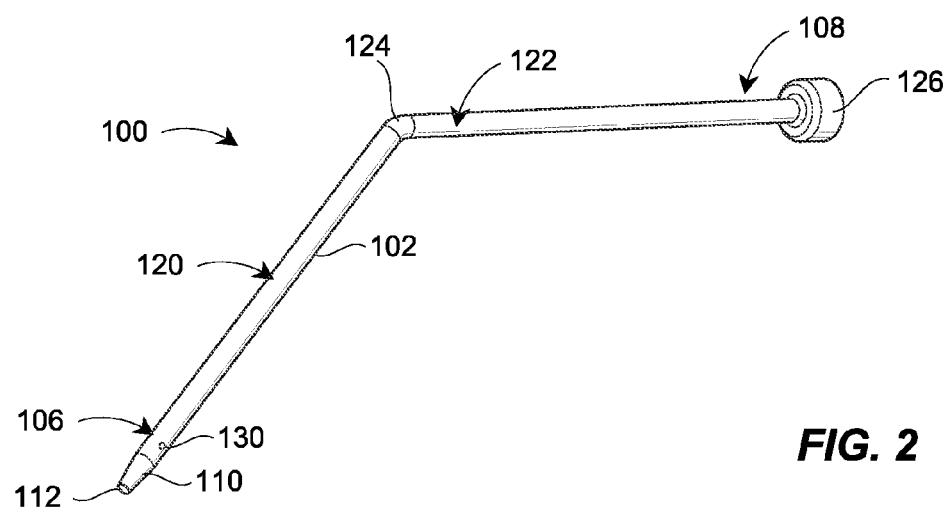
FIG. 2 is a perspective view of an embodiment of a blunt cannula according to the present disclosure that may be used with a drug delivery device, such as is illustrated in FIG. 1, with at least one pair of side ports.
Figure 5:
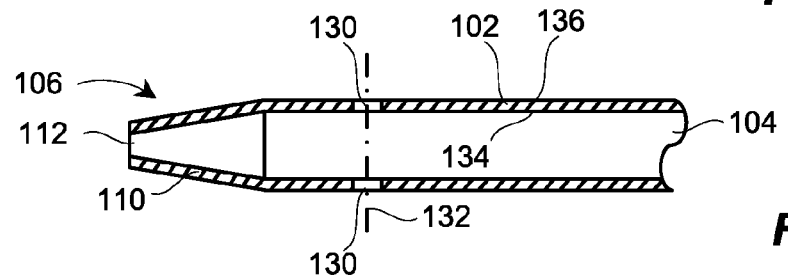
FIG. 5 is a cross-sectional view of the blunt cannula of FIG. 4 taken along line 5-5.

FIG. 2 illustrates a blunt cannula 100, corresponding to the blunt cannula 54 in FIG. 1, having a cylindrical wall 102 that defines an axial passage 104 best seen in FIG. 5. The axial passage 104 extends between a first end 106 and a second end 108 of the blunt cannula 100. The wall 102 has at least a first tapered region 110 at the first end 106 to define an opening 112 in fluid communication with an axial passage 104.

Figure 3:
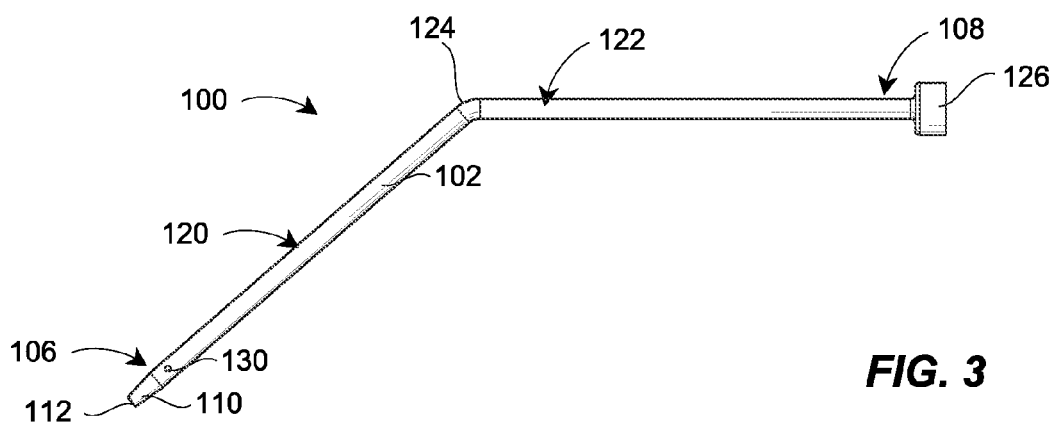
FIG. 3 is a side view of the blunt cannula of FIG. 2.
Figure 4:
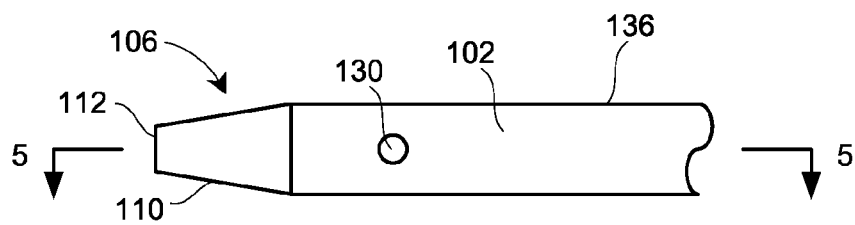
FIG. 4 is an enlarged side view of a first end of the blunt cannula of FIG. 2.

As regards the specific embodiment of the blunt cannula 100 illustrated in FIG. 2, it will be recognized that the cannula 100 includes a first segment 120 and a second segment 122 that are connected by a joint or transition 124. The first segment 120 and the second segment 122 are disposed at an angle to each other, as best seen in FIG. 3. According to the illustrated embodiment, the first segment 120 and the second segment 122 are disposed at an obtuse angle relative to each other. Even though the segments 120, 122 are disposed at an angle to each other, the passage 104 may still be referred to as the axial passage. Moreover, while FIGS. 1 and 2 show a cannula with segments disposed at an angle to each other, there may be additional embodiments where the segments are not at an angle to each other and the cannula could in fact be a single straight segment.

In some embodiments, a hub 126 is disposed at the second end 108 of the cannula 100, while in other embodiments a hub may not be present. The hub 126 may surround a needle 58 or other connector used to connect the cannula 100 with a reservoir such that the cannula 100 and the reservoir are in fluid communication with each other (e.g., by having the needle 58 pierce a rubber septum or the like). While the structure has been explained in regard to the illustrated embodiment, the cannula according to the present disclosure is not so limited, and variations may exist to the cannula illustrated in FIGS. 2 and 3.

The first end 106 also is adapted to resist interruption of fluid flow through the axial passage 104 and out of the first end 106 of the blunt cannula 100. As will be discussed in regards to the remaining embodiments, the manner in which the first end 106 is adapted to resist interruption of fluid flow may vary. In fact, while a variety of adaptations are discussed individually in regards to FIG. 2-15, it will be appreciated that it is possible to combine the specific embodiments discussed in each of the illustrations of FIGS. 2-15 with each other. For example, the embodiments of FIGS. 2-5 or FIG. 6 may be combined with the embodiment of FIG. 7. Still further combinations will be apparent to those skilled in the art, and discussed below.

As to the adaptation illustrated in FIGS. 2-5, this embodiment has at least one pair of side ports 130 formed in the wall 102 of the blunt cannula 100 at the first end 106, although the present disclosure would also encompass an embodiment that includes at least one side port (e.g., only one side port). The at least one pair of side ports 130 illustrated in FIGS. 2-5 are in the form of circular openings formed in the wall 102 of the blunt cannula 100 at the first end 106. Further, as best seen in FIG. 5, the circular openings formed in the wall 102 of the blunt cannula 100 are aligned with each other across the axial passage 104 (i.e., the circular openings lie along a transverse axis 132), however such alignment is not necessary. For example, the side ports 130 may be at different distances from the first end 106 of the cannula 100.

In regard to the two side ports 130, it will be recognized that the wall 102 of the blunt cannula 100 has an internal surface 134 and an external surface 136. The side ports 130 have a first opening on the internal surface 134 and a second opening on the external surface 136, and a passage connecting the first and second openings. Consequently, the side ports 130 depend through the wall 102 of the cannula 100.

As will be further recognized, the side ports 130 of the embodiment illustrated in FIGS. 2-5 are formed in the first end 106 of the blunt cannula 100 distal from the first tapered region 110 that defines the opening 112. In other embodiments, the side ports 130 may be disposed within the first tapered region 110. In still other embodiments, the side ports 130 are disposed further from the first tapered region 110.

According to a specific embodiment of the present disclosure, the side ports may have a diameter of 0.006 inches (0.15 mm), and may be disposed 0.06 inches (1.5 mm) from the opening 112 for a 24 gauge cannula. In an alternative embodiment, the side ports may have a diameter of 0.006 inches (0.15 mm), and may be disposed 0.08 inches (2 mm) from the opening 112 for a 24 gauge cannula. In yet other embodiments the diameter and the distance from the opening 112 may be different than the values set forth immediately above. The ports may be formed using a drill, for example.

Figure 6:
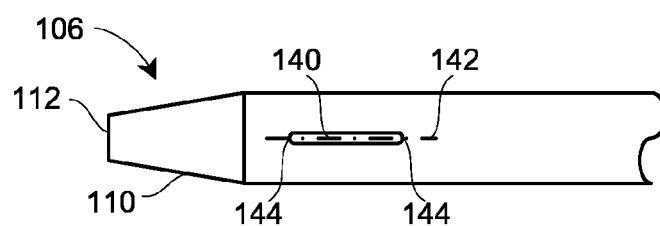
FIG. 6 is an enlarged side view of a first end of another embodiment of a blunt cannula according to the present disclosure with at least one pair of side ports having a different shape than those of FIGS. 2-5.

FIG. 6 illustrates a related embodiment of the present disclosure wherein at least one pair of side ports is formed in the wall 102 of the blunt cannula 100. However, unlike the embodiment illustrated in FIGS. 2-5, the embodiment of the side port illustrated in FIG. 6 is in the form of an elongated slit or an elongated slot 140 (wherein the slit has a narrow width relative to the slot). Specifically, the elongated slit 140 may lie along an axis 142 that runs parallel to the axial passage 104. Further, the elongated slit 140 may have first and second rounded ends 144. As was the case relative to the side ports 130, the slits 140 may have in a first opening in the internal surface 134 and a second opening in the external surface 136 of the blunt cannula 100, and a passage connecting the first and second openings. The slit may be formed using laser cutting tools, for example.

Figure 7:
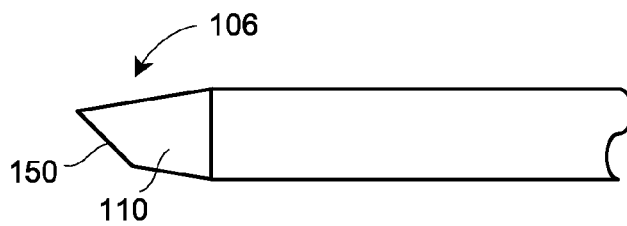
FIG. 7 is an enlarged side view of a first end of another embodiment of a blunt cannula according to the present disclosure with a single bevel.
Figure 8:
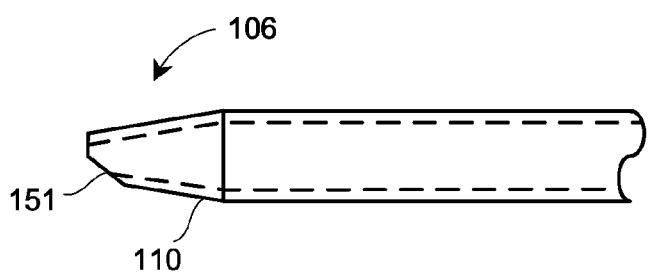
FIG. 8 is an enlarged side view of a first end of another embodiment of a blunt cannula according to the present disclosure with a single offset bevel.
Figure 9:
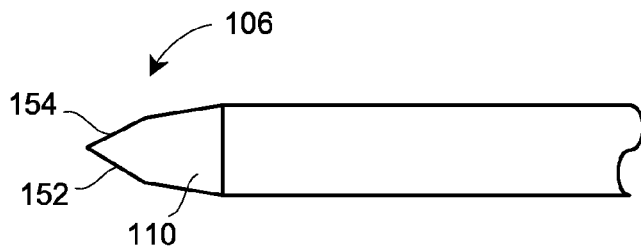
FIG. 9 is an enlarged side view of a first end of another embodiment of a blunt cannula according to the present disclosure with a pair of positive, intersecting bevels.
Figure 10:
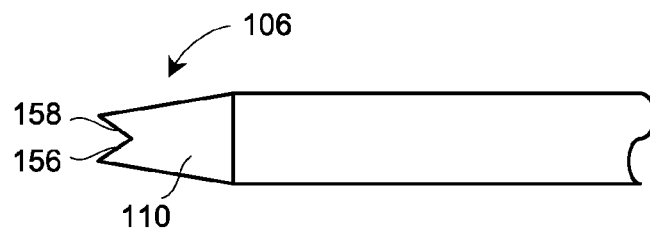
FIG. 10 is an enlarged side view of a first end of another embodiment of a blunt cannula according to the present disclosure with a pair of negative, intersecting bevels.

FIGS. 7-9 illustrate a different adaptation for resisting the interruption of fluid flow through the axial passage 104. In particular, the embodiments illustrated in FIGS. 7-9 involve the formation of at least one bevel in the first end 106 of the cannula 100. In particular, the at least one bevel is formed in the first tapered region 110 that defines the opening 112. As a consequence, whereas the opening 112 illustrated in the embodiments of FIGS. 2-6 may be circular in cross-section, the opening 112 of the embodiments illustrated in FIGS. 7-10 may have at least one oblong or oval face, and may in fact have oval faces in multiple planes inclined relative to the axial passage 104.

In particular, the embodiments illustrated in FIGS. 7 and 8 include only a single bevel 150, 151, although the embodiment of FIG. 7 has the bevel across the entire tapered region 110 while the embodiment of FIG. 8 has the bevel across only a portion of the tapered region 110 (which may make the end of the embodiment of FIG. 8 more resistant to buckling or bending as a consequent). The bevel 150, 151 may be referred to as a positive bevel herein. In a similar vein, FIG. 9 illustrates the use of two positive bevels 152, 154 intersecting each other. However, it is also possible to use an inverted or negative bevel, as is done in FIG. 10 wherein an inverted double bevel 156, 158 is used. As mentioned previously, any one of the embodiments illustrated in FIGS. 7-10 may be used with any one of the embodiments illustrated in FIGS. 2-6 in so far as the side ports do not interfere with the function of the bevel or bevels formed in the tapered region 110.

As illustrated, the bevel may be inclined at 45 degrees. However, it will be recognized that other angles of bevel are possible. It will also be recognized that shallow angles resist buckling of the blunt cannula when the cannula is inserted into or through the skin of the patient.

Figure 11:
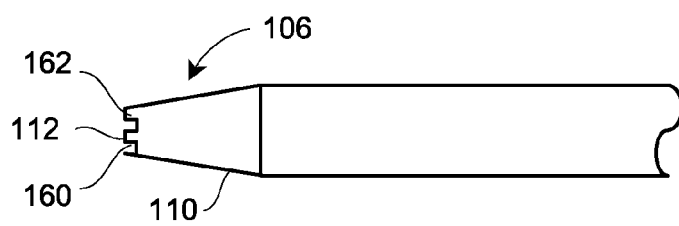
FIG. 11 is an enlarged side view of a first end of another embodiment of a blunt cannula according to the present disclosure with a first pattern of recesses disposed about an axial opening.
Figure 12:
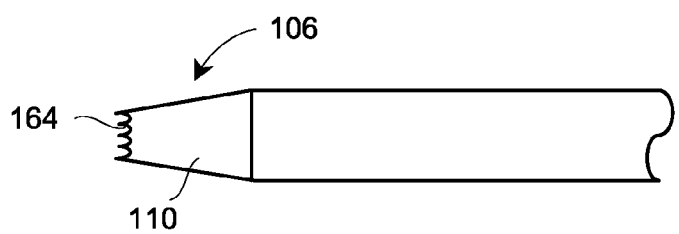
FIG. 12 is an enlarged side view of a first end of another embodiment of a blunt cannula according to the present disclosure with a second pattern of recesses disposed about an axial opening.
Figure 13:
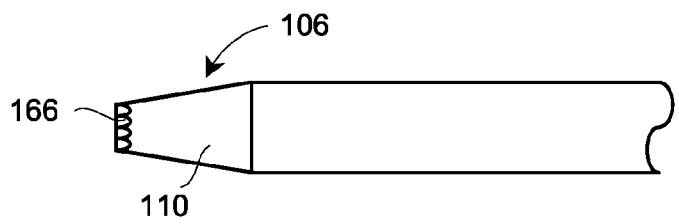
FIG. 13 is an enlarged side view of a first end of another embodiment of a blunt cannula according to the present disclosure with a pattern of transverse openings disposed about a capped first end.

FIGS. 11-13 illustrate further adaptations for resisting the interruption of fluid flow through the axial passage 104. In particular, the embodiments illustrated in FIGS. 11-13 involve a pattern of openings disposed about the opening 112 in the first tapered region 110. The pattern of openings may be regular and periodic as illustrated, or the pattern of openings may be irregular (i.e., the spacing may not be equal relative to the openings and the intervening wall sections).

For example, the embodiment of FIG. 11 includes a regular and periodic pattern of openings 160 and wall sections 162. The resulting pattern may be referred to as castellated. Similarly, a second pattern of openings 164 is illustrated in FIG. 12, which openings 164 may be defined as recesses in the tapered region 110 formed by a series of grooves transverse to the axial passage 104. In fact, a still further pattern of openings 166 is illustrated in FIG. 13, wherein the first end 106 is capped such that fluid flow is only possible transverse to the axial passage 104 through the openings 166. The openings 166 may be referred to as windows.

As was the case relative to the embodiments illustrated in FIGS. 7-10, the embodiments illustrated in FIGS. 11-13 may be used in combination with any of the embodiments illustrated in FIGS. 2-5. Alternatively, the embodiments illustrated in FIGS. 11-13 may be used in combination with any of the embodiments illustrated in FIGS. 7-10. Still further, the embodiments illustrated in FIGS. 11-13 may be used in combination with the embodiments of FIGS. 2-6 and 7-10.

Figure 14:
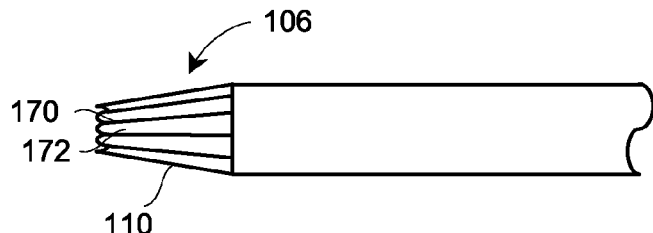
FIG. 14 is an enlarged side view of a first end of another embodiment of a blunt cannula according to the present disclosure with having recessed surface regions on an external surface of the cannula defined by a pattern of ribs formed on the external surface.
Figure 15:
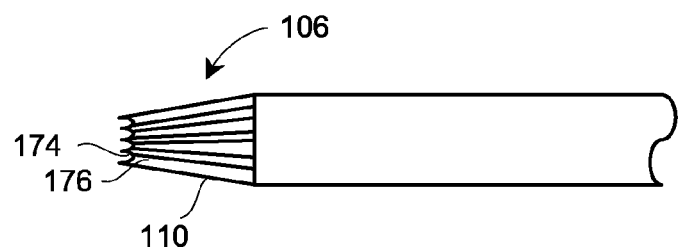
FIG. 15 is an enlarged side view of a first end of another embodiment of a blunt cannula according to the present disclosure with having recessed surface regions on an external surface of the cannula defined by a pattern of grooves formed in the external surface.

FIGS. 14 and 15 illustrate still further adaptations for minimizing or reducing the interruption of fluid flow through the axial passage 104 as well as resisting buckling of the cannula 100. In particular, the wall 102 of the blunt cannula 100 may have at least one external recessed region formed thereon, the recess being recessed towards the axial passage 104 relative to adjoining surface regions. This at least one external recessed region may be in a pattern that is both regular and periodic, or the pattern of openings may be irregular (i.e., the spacing may not be equal relative to the first tapered region 110).

According to the embodiment illustrated in FIG. 14, the at least one recessed region 170 may be defined by a pattern of ribs 172 formed on the external surface 136. Alternatively, the least one recessed region 174 in FIG. 15 may be defined by a pattern of grooves 176 formed in the external surface 136. It may also be possible to define the least one recessed region using the combination of a pattern of ribs and a pattern of grooves in combination. It is preferred that the ribs or grooves terminate before the portion of the cannula 100 that depends from the insertion site so as to limit the possibility of leakage from the site. It is also preferred that the ribs or grooves be used with at least one side port or opening along the perimeter of the opening 112, although the ribs or grooves may be used without providing a side port or other opening (e.g., with a beveled end).

As was the case relative to the embodiments illustrated above, the embodiments illustrated in FIGS. 14 and 15 may be used in combination any one of the embodiments illustrated in FIGS. 2-13. It is the case that the embodiments of FIGS. 14 and 15 may be most useful with an embodiment where a radial flow path is provided, such as with the provision of a side port, tip groove, or the like. Alternatively, the embodiments illustrated in FIGS. 14 and 15 may be used in combination with any of the embodiments illustrated any one or more of the groups of adaptations in FIG. 2-6, 7-10 or 11-13. Consequently, the embodiments illustrated in FIGS. 14 and 15 may be used in combination with embodiments section from each of the groups illustrated in FIGS. 2-6, 7-10, and 11-13.

Figure 16:
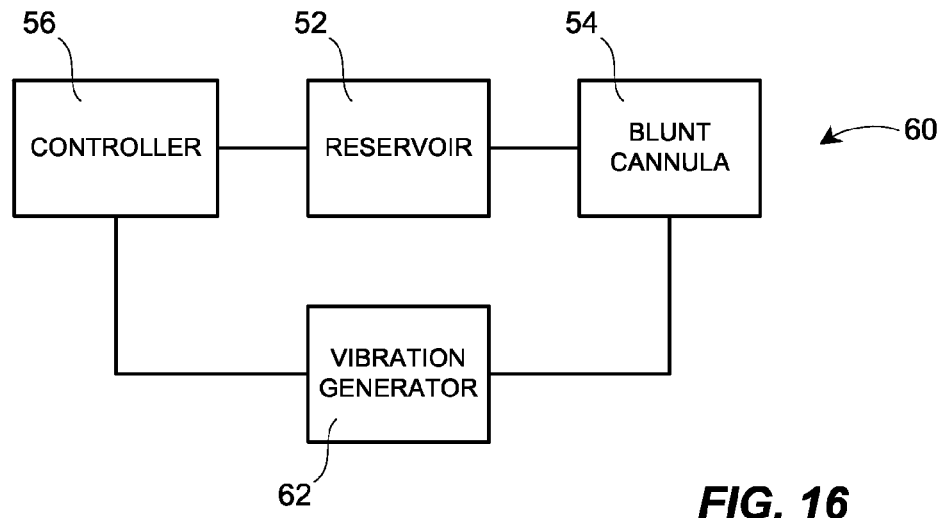
FIG. 16 is a schematic view of a drug delivery device according to the present disclosure, including a blunt cannula (which may or may not have features of the blunt cannulas illustrated in FIGS. 2-15) and a vibration generator.

A still further adaptation according to the present disclosure is illustrated in FIG. 16. According to this embodiment, in addition to the reservoir 52, cannula 54, and controller 56, the drug delivery device 60 includes a vibration generator 62. The operation of the vibration generator 62 may be controlled by the controller 56 to which it is operatively coupled. In addition, the output of the vibration generator 62 may be operatively coupled to the cannula 54. The vibration generator may be in the form of a motor having a shaft with an eccentric weight attached to the shaft. Alternatively, the vibration generator may be in the form of a piezoelectric vibrator. Still further alternative embodiments are possible. Actuation of the vibration generator 62 may dislodge an obstruction or blockage from the end of the cannula 54, move the tip of the cannula 54 away from the occluding structure (e.g., tissue), or create a pocket of micro-fractured tissue increasing the surface area for lower pressure threshold, thereby permitting flow to resume As was the case with the adaptations recited above, the adaptation illustrated in FIG. 16 may be used with any one or more of the adaptations illustrated in FIGS. 2-15.

In addition, while the previous embodiments have been discussed in regard to a blunt cannula, certain of the above-mentioned adaptations may also be used with a rigid needle as well, which needle may be made of metal and have a point defined by one or more bevels made at a first end of the needle. The rigid needle may have a cylindrical wall that defines a passage between the first end and a second end, and the first end may have an opening that is in fluid communication with the axial passage. Moreover a reservoir may be connected to the second end of the rigid needle.

In particular, the adaptations according to FIGS. 11, 12 and 14-16 may be used with the rigid needle.

As will be recognized, the devices according to the present disclosure may have one or more advantages relative to conventional technology, any one or more of which may be present in a particular embodiment in accordance with the features of the present disclosure included in that embodiment. In particular, each of the embodiments illustrated in FIGS. 2-15 provides alternative flow paths for the drug product should the opening in the first end of the blunt cannula be obstructed or blocked, thereby limiting the possibility of the interruption of the flow through the cannula. The embodiments also increase the surface area exposed, lowering the pressure threshold required to displace tissue. The embodiment illustrated in FIG. 16 uses a different mechanism by which to limit the interruption of flow through the cannula, wherein the vibrations may dislodge an obstruction or blockage from the end of the cannula, move the cannula tip away from the occluding structure (e.g., tissue), or create a pocket of micro-fractured tissue increasing the surface area for lower pressure threshold, thereby permitting flow to resume. Other advantages not specifically listed herein may also be recognized as well.

FIGS. 17-20 illustrate how the systematic approach to lowering the pressure required to pass fluid through a cannula or needle provided by the embodiments according to the present disclosure may operate in a particular application of this technology. In particular, this discussion is in relation to a wearable drug delivery device, which is one that is attached to the patient's skin and includes its own mechanism(s) for deploying the cannula or needle and delivering fluid through that cannula or needle. Because a wearable drug delivery device (e.g., autoinjector, infuser or microinfuser) has a generally limited ability to increase the pressure at which a fluid is delivered to the patient, a variable increase in the pressure required to pass fluid through the cannula or needle into the tissue may unpredictably reduce the amount of fluid (e.g., drug) delivered to the patient or may require that the device be engineered to provide higher pressures, which pressures may not always be required. Consequently, a systematic approach to reducing the pressure required to deliver fluid through the cannula or needle may not only limit the need to engineer such a delivery device to provide higher pressures, it may ensure that a specific amount of fluid is consistently provided to the patient, improving the reliability of the device.

Figure 17:
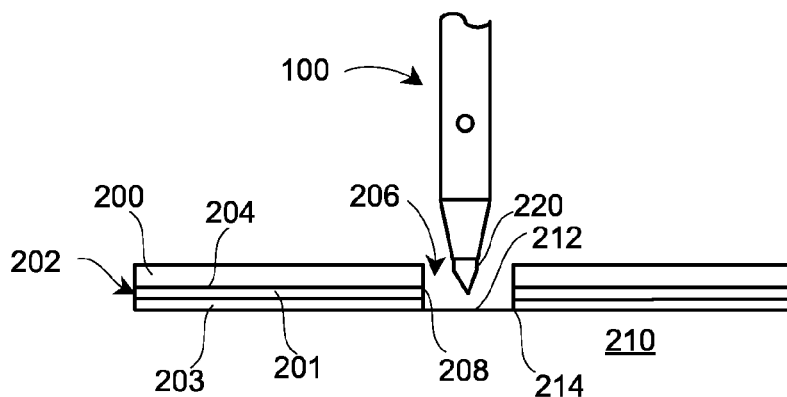
FIG. 17 is an enlarged schematic view of a drug delivery device according to the present disclosure and a region of skin to which the drug delivery device is applied.

In particular, the resistance to fluid flow in such a wearable device may come about as a consequence of an effect referred to herein as "tenting" As illustrated in FIG. 17, a wearable drug delivery device has a housing 200 with an adhesive layer 202 disposed on an outer surface 204 of the housing 200, which adhesive layer 202 may include a fabric backing 201 and an adhesive 203 according to certain embodiments. See FIG. 17 (while not specifically illustrated in FIGS. 19 and 20, the adhesive layer 202 in these Figs. may be defined as illustrated in FIG. 17 as well). In particular, the adhesive layer 202 is disposed on the housing 200 except for a region 206 disposed about the cannula or needle 100 (which, as illustrated, is similar to the embodiment illustrated in FIGS. 2-5). This region 206 may be referred to as adhesive-free, and according to those embodiments wherein the adhesive layer 202 includes both a fabric backing 201 and an adhesive 203, the region 206 would be free of both the backing and the adhesive while still termed "adhesive-free."

For example, the region 206 may be adhesive-free in that an opening 208 is formed in the housing 200. According to certain embodiments, the opening 208 may be made as small as is possible while still providing for the free passage of the cannula 100. For example, according to one embodiment, the opening 208 is circular and has a diameter that is not more than twice the diameter of the cannula 100 (by which phrase it is also understood that the opening 208 must be greater than the diameter of the cannula 100 or rigid needle so that the cannula or rigid needle may be disposed through the opening 208 in an operative state of the wearable device and the cannula 100).

Figure 18:
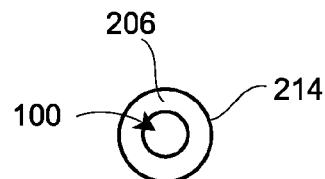
FIG. 18 is an enlarged plan view of the region of skin illustrated in FIG. 17, with a point of introduction or insertion of the cannula or needle illustrated relative to a region of skin to which the drug delivery device is applied with adhesive.

While the skin 210 (and associated subcutaneous tissue) to which the drug delivery device is attached has some degree of elasticity (which elasticity may vary from person to person), the adhesive layer 202 disposed about the region 206 attaches the device (and in particular, the housing 200) to the skin surface 212 so as to hold the skin surface 212 at a boundary 214 substantially fixed relative to the housing 200 (see also FIG. 18). While there may be some movement at or along this boundary 214, it is not substantial. As a consequence, when the cannula or needle 100 is automatically advanced or deployed by the action of the drug delivery device in the direction of the skin surface 212, the skin surface 212 starts to stretch relative to the fixed boundary 214. Furthermore, as the cannula or needle 100 passes through the skin 210, the insertion of the cannula 100 causes dragging of the skin tissue 210 because of friction between the cannula 100 and the skin 210. This causes a "tenting" action to occur about the cannula or needle 100 as illustrated in FIG. 19 with reference to numeral 216.

Figure 19:
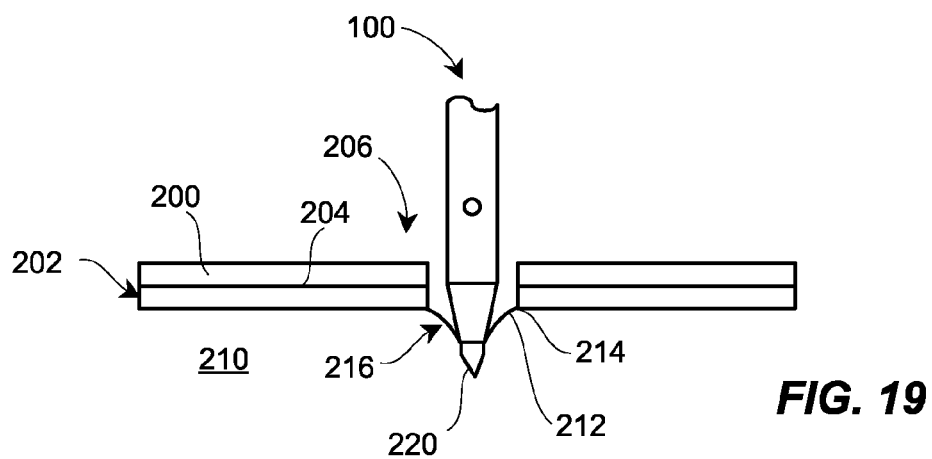
FIG. 19 is an enlarged schematic view of the drug delivery device of FIG. 17 in an intermediate state or configuration as the cannula or needle is introduced into the skin.
Figure 20:
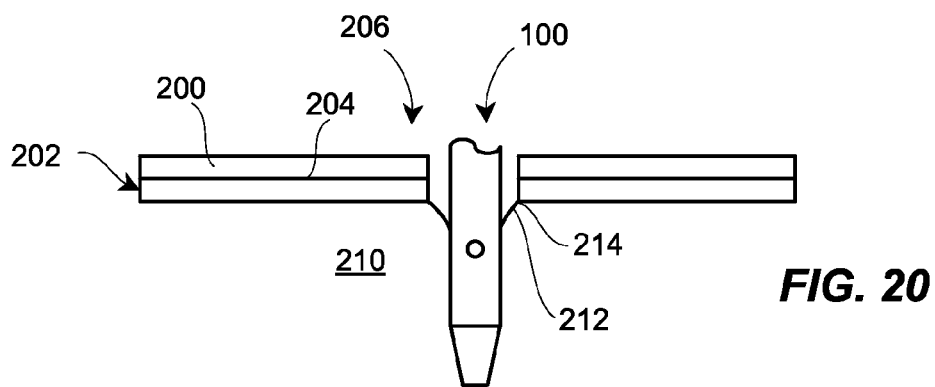
FIG. 20 is an enlarged schematic view of the drug delivery device of FIG. 17 in a final state or configuration with the cannula or needle fully introduced or inserted into the skin.

As a brief aside, it will be recognized that the cannula 100 in FIGS. 17-20 is illustrated disposed about a structure that is used to insert the cannula into the skin, and which may be removed thereafter to permit fluid to pass through the cannula (compare FIGS. 19 and 20). This structure, which may be referred to as an introducer needle 220, need not be present in all embodiments according to the present disclosure. However, according to certain embodiments, the introducer needle 220 is disposed in the cannula 100 and is used to introduce the cannula 100 into the skin 210, after which it may be removed from cannula 100 (see FIG. 20).

As illustrated in FIG. 20, the cannula 100 has now been inserted into the skin 210, and the surface 212 of the skin 210 has generally attempted to return to its original position relative to the outer surface 204 of the drug delivery device housing 200. However, the friction between the cannula 100 and the skin tissue 210 prevents the tissue from completely returning to its initial, or rest, state. As such, the residual forces of the skin and subcutaneous tissues against the tip of the cannula 100 increases the pressure required to deliver fluid through the tip of the cannula 100, and may completely obstruct the tip of the cannula 100 as well.

According to any of the embodiments of the cannula or needle in FIGS. 2-15, the pressure required to pass fluid into the tissue may be reduced by, for example, increasing the overall surface area of tissue exposed to the fluid, through the introduction of side ports, etc. In addition, by vibrating the tissue, according to the mechanism of FIG. 16, some of the residual force in the skin tissue 210 may be released, thereby decreasing the pressure and potential for occlusion. The embodiments of FIGS. 2-15 may be used in combination with the vibration provided by the embodiment of FIG. 16, or the embodiments of FIGS. 2-15 and 16 may be used separately. In any event, it is believed that the embodiments disclosed herein may provide a solution to the tenting of the skin caused at the time the cannula or needle is automatically introduced or deployed into the patient by a wearable drug delivery device. It is also believed that by reducing the size of the opening (fenestration) 208 in the adhesive layer 202, there will be a reduction in tenting and associated residual forces.

As also mentioned above, the reservoir 52 may be filled with a drug or pharmaceutical product. For example, the reservoir may be filled with colony stimulating factors, such as G-CSF. Such G-CSF agents include, but are not limited to, Neupogen® (filgrastim) and Neulasta® (pegfilgrastim).

In various other embodiments, the drug delivery device may be used with various pharmaceutical products, which use may or may not occur under the same conditions as described above for G-CSF. These products may include, for example, an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/03742 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C 10, chimaeric antibody C7C 10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-

1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/068,289, which is incorporated herein by reference in its entirety, particularly in parts pertinent to proteins that bind OX40L and/or other ligands of the OXO40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4137 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a);

Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

We claim:

1. A wearable on-body drug delivery device comprising:
a housing having an opening;
an adhesive layer attached to a surface of the housing for attaching the drug delivery device to a patient's skin;
a reservoir disposed in the housing, the reservoir including a barrel;
a plunger movably disposed in the barrel;
a volume of a drug product disposed in the reservoir, the drug product comprising a granulocyte colony-stimulating factor (G-CSF);
a first needle;
a cannula or second needle having a cylindrical wall that defines an axial passage between a first end and a second end of the cannula or second needle, the first end of the cannula or second needle being initially retracted within the housing and subsequently deployed through the opening in the housing for insertion into the patient's skin, the second end of the cannula or second needle configured to be operably connected in fluid communication with the reservoir via the first needle, wherein the first needle does not penetrate the patient's skin during insertion of the first end of the cannula or second needle into the patient's skin;
a drive operably coupled to the reservoir to urge the drug product from the reservoir, through the cannula or second needle, and to a patient during use of the drug delivery device; and
wherein the wearable on-body drug delivery device is free of an introducer needle for introducing the cannula or second needle into the patient's skin.

2. The drug delivery device according to claim 1, wherein the cannula or second needle has at least one side port formed in the wall of the cannula or second needle at the first end.

3. The drug delivery device according to claim 2, wherein the at least one side port comprises a pair of side ports.

4. The drug delivery device according to claim 3, wherein the pair of side ports are aligned with each other across the axial passage.

5. The drug delivery device according to claim 2, wherein the at least one side port comprises a circular opening formed in the wall to permit flow transverse to the axial passage.

6. The drug delivery device according to claim 2, wherein the at least one side port comprises an elongated slit formed in the wall to permit flow transverse to the axial passage.

7. The drug delivery device according to claim 2, wherein the at least one side port comprises an elongated slot formed in the wall to permit flow transverse to the axial passage.

8. The drug delivery device according to claim 2, wherein the first end of the cannula or second needle includes a first tapered region, and wherein the at least one side port is formed in the first end of the cannula or second needle distal from the first tapered region.

9. The drug delivery device according to claim 1, wherein the first end of the cannula or second needle includes a first tapered region that comprises at least one bevel.

10. The drug delivery device according to claim 9, wherein the first tapered region comprises only one bevel.

11. The drug delivery device according to claim 9, wherein the first tapered region comprises two bevels intersecting each other.

12. The drug delivery device according to claim 9, wherein the first tapered region comprises two negative or inverted bevels intersecting each other.

13. The drug delivery device according to claim 9, wherein the first end of the cannula or second needle includes a pattern of openings disposed about an opening in the first tapered region.

14. The drug delivery device according to claim 13, wherein the pattern of openings comprises a pattern of recesses into the wall.

15. The drug delivery device according to claim 1, wherein the cannula or second needle has at least one external recessed region recessed toward the axial passage relative to adjoining surface regions.

16. The drug delivery device according to claim 15, wherein the at least one external recessed region is defined by a pattern of ribs.

17. The drug delivery device according to claim 15, wherein the at least one external recessed surface region is defined by a pattern of grooves.

18. The drug delivery device of claim 1, comprising a hub surrounding at least a portion of the first needle.

19. The drug delivery device of claim 18, wherein the hub is positioned adjacent to the second end of the cannula or second needle.

* * * * *